United States Patent [19]
Oertle

[11] 3,949,593
[45] Apr. 13, 1976

[54] DIFFUSION MONITORING APPARATUS
[75] Inventor: Donald H. Oertle, Ponca City, Okla.
[73] Assignee: Continental Oil Company, Ponca City, Okla.
[22] Filed: Mar. 7, 1975
[21] Appl. No.: 556,237

[52] U.S. Cl. .......................................... 73/19; 73/53
[51] Int. Cl.² .......................................... G01N 7/10
[58] Field of Search ................... 73/19, 23, 61.2, 53

[56] References Cited
UNITED STATES PATENTS
3,683,272  8/1972  Vissers et al. ..................... 73/19 X
3,731,523  5/1973  Vissers et al. ..................... 73/19

FOREIGN PATENTS OR APPLICATIONS
2,035,817  1/1972  Germany ............................. 73/23

Primary Examiner—Richard C. Queisser
Assistant Examiner—Joseph W. Roskos
Attorney, Agent, or Firm—F. Lindsey Scott

[57] ABSTRACT

Apparatus for connecting the open end of an elongated hollow probe member to a chamber whereby the interiors of the probe member and the chamber can be evacuated while the probe member and chamber are disconnected from each other and then the probe member sealingly connected to the chamber while maintaining the evacuation.

13 Claims, 5 Drawing Figures

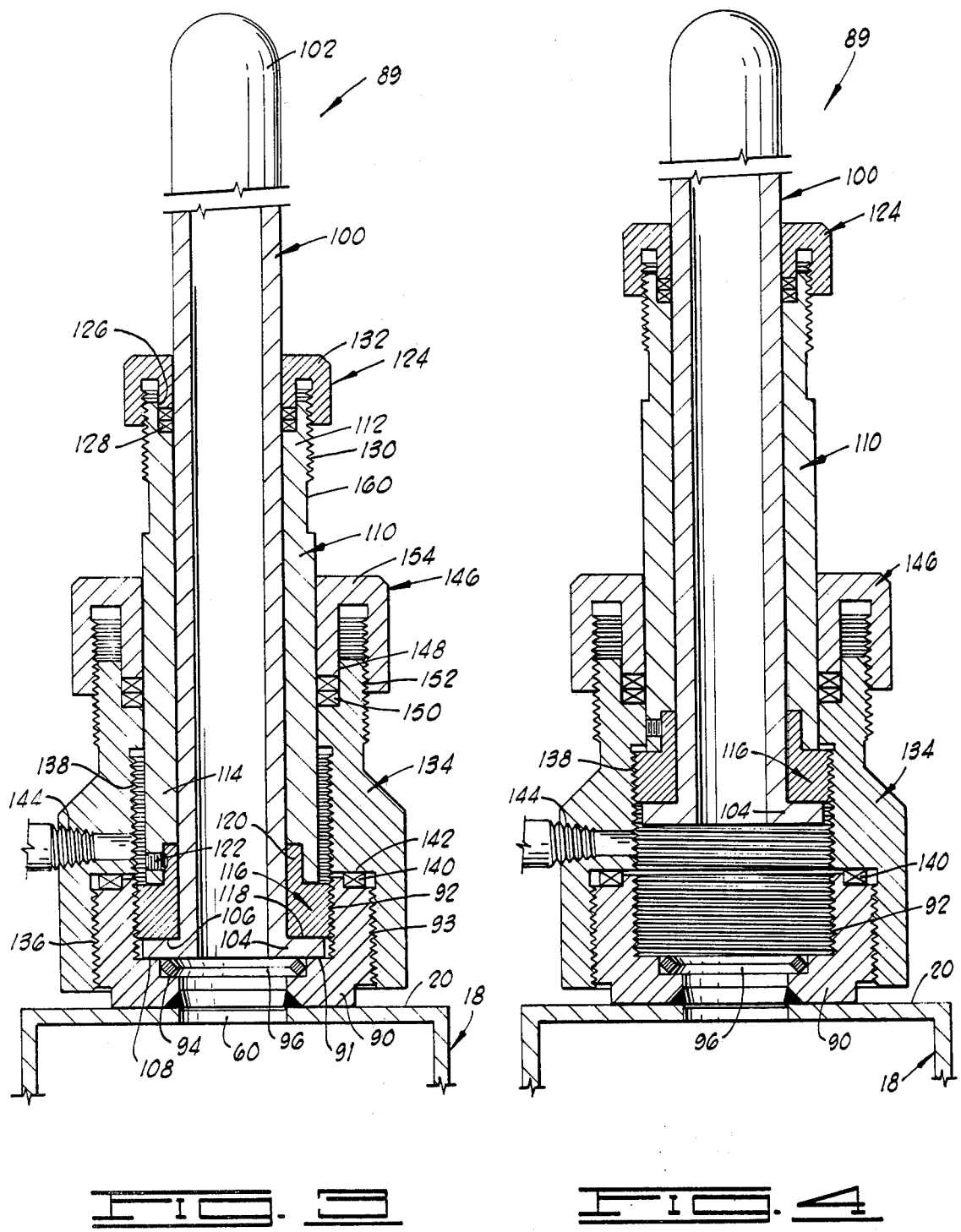

DIFFUSION MONITORING APPARATUS

BACKGROUND OF THE INVENTION

1. Field of the Invention

This invention relates generally to an improved diffusion monitoring apparatus, and more particularly, but not by way of limitation, to improved diffusion monitoring apparatus of the type including an evacuated hollow diffusion probe member connected to an evacuated collector chamber.

2. Description of the Prior Art

Apparatus for monitoring selected components of a fluid system whereby the selected components diffuse through a probe have heretofore been developed and used successfully. Generally, such monitoring apparatus include an evacuated elongated hollow probe member through which the components to be monitored diffuse, a closed evacuated collector chamber sealingly connected to the probe member and an ion pump means utilized as a collector chamber for providing an electrical current output in proportion to the rate of diffusion of the selected components. Such monitoring apparatus are especially useful in monitoring atomic hydrogen permeation of a steel probe exposed to a corrosive fluid, which hydrogen permeation indicates corrosion of the steel probe exposed to the fluid. The monitoring apparatus can be used to control the injection of inhibitor into the fluid system or to control other process variables so that corrosion in the system is maintained at a minimum.

In operation of such heretofore used diffusion monitoring apparatus, the probe member is formed of a selected material which allows the diffusion of one or more selected components from a fluid system. The probe member is connected to a collector chamber which is attached to an ion pump, and both the interior of the probe and the interior of the collector chamber are evacuated. While the probe can take a variety of configurations, it usually is comprised of an elongated hollow member closed at one end and sealingly connected to the collector chamber at the other end. The collector chamber includes a port communicating the interior of the chamber with the interior of the probe and an ion pump is contained in or connected to the other end of the chamber. The ion pump functions as a trap in which the selected components are ionized and accelerated by high electrical potential into an electrode where the component is buried or gettered, thus removing it from the collector chamber. As gases are trapped their presence is detected as a current differential exceeding a predetermined background value which can be read by a meter or utilized in a variety of control apparatus.

Heretofore, in order to evacuate the interior of the probe and collector chamber, the probe or collector chamber have been provided with a port connected to a shutoff valve (commonly referred to as a roughing valve) by conduit means. When starting up the monitoring apparatus, the shutoff valve is connected to a rough vacuum pump and the probe, collector chamber and ion pump evacuated thereby. After the evacuation has reached the point that the ion pump begins to operate the shutoff valve is closed and the rough vacuum pump disconnected therefrom. The use of such a shutoff valve with diffusion monitoring apparatus often constitutes a problem due to leakage of air through the valve into the probe and collector chamber brought about by wearout of the valve or the accidental opening of the valve thereby causing the vacuum to be lost and operation of the apparatus to be interrupted. Further, the use of such a shutoff valve adds to the overall cost of the apparatus.

By the present invention an improved diffusion monitoring apparatus is provided which obviates the requirement for a vacuum shutoff valve and the problems and expense attendant therewith as well as resulting in a smaller less bulky unit.

SUMMARY OF THE INVENTION

The present invention relates to an improved diffusion monitoring apparatus which includes an evacuated elongated hollow probe member through which selected components to be monitored diffuse, a closed evacuated collector chamber sealingly connected to the rearward end of the probe member and an ion pump means attached to the collector chamber for providing an electrical current output in proportion to the rate of diffusion of the selected components. By the invention, the collector chamber includes a port for communicating the interior thereof with the interior of the probe member, and a cylindrical connection member is sealingly attached to the collector chamber over the port, the connection member having threads disposed around the outside periphery thereof and within the interior thereof. The rearward end of the probe member is of a size and includes threads disposed thereon for threadedly engaging the threads within the interior of the connection member. A housing is provided having a forward end and a rearward end, the rearward end including a threaded opening adapted to threadedly engage the threads disposed around the outside periphery of the connection member and the forward end including an opening therein through which the probe member is slidably disposed whereby the probe member can be threadedly connected to the connection member from the exterior of the housing. The housing further includes an opening therein for connection to vacuum pump means so that the housing, the collector chamber and the probe member can be evacuated with the probe member disconnected from the connection member, the probe member then threadedly connected to the connection member while maintaining the evacuation and the housing subsequently removed from the connection member and the probe member. Means are disposed in the opening in the forward end of the housing for providing a sliding seal between the housing and the outside peripheral surfaces of the probe member.

It is, therefore, a general object of the present invention to provide an improved diffusion monitoring apparatus.

A further object of the present invention is the provision of an improved diffusion monitoring apparatus which does not require a vacuum shutoff valve and which eliminates the problems and expense attendant therewith.

A further object of the present invention is the provision of an improved diffusion monitoring apparatus including a housing or manifold which can be temporarily connected to the diffusion probe and collector chamber, utilized to evacuate the interiors of the probe member and collector chamber while the probe member is disconnected from the collector chamber and during the connection thereof and then removed from the probe member and collector chamber to provide a smaller neater monitoring unit.

Other and further objects, features and advantages of the present invention will be readily apparent to those skilled in the art upon a new reading of the description of preferred embodiments which follows taken in conjunction with the accompanying drawings.

BRIEF DESCRIPTION OF THE DRAWINGS

FIG. 3 is an enlarged side cross-sectional view of an alternate embodiment of the present invention showing the probe in the connected position;

FIG. 4 is an enlarged side cross-sectional view of the apparatus of FIG. 3 showing the probe member disconnected from the collector chamber.

DESCRIPTION OF PREFERRED EMBODIMENTS

Figure 1:
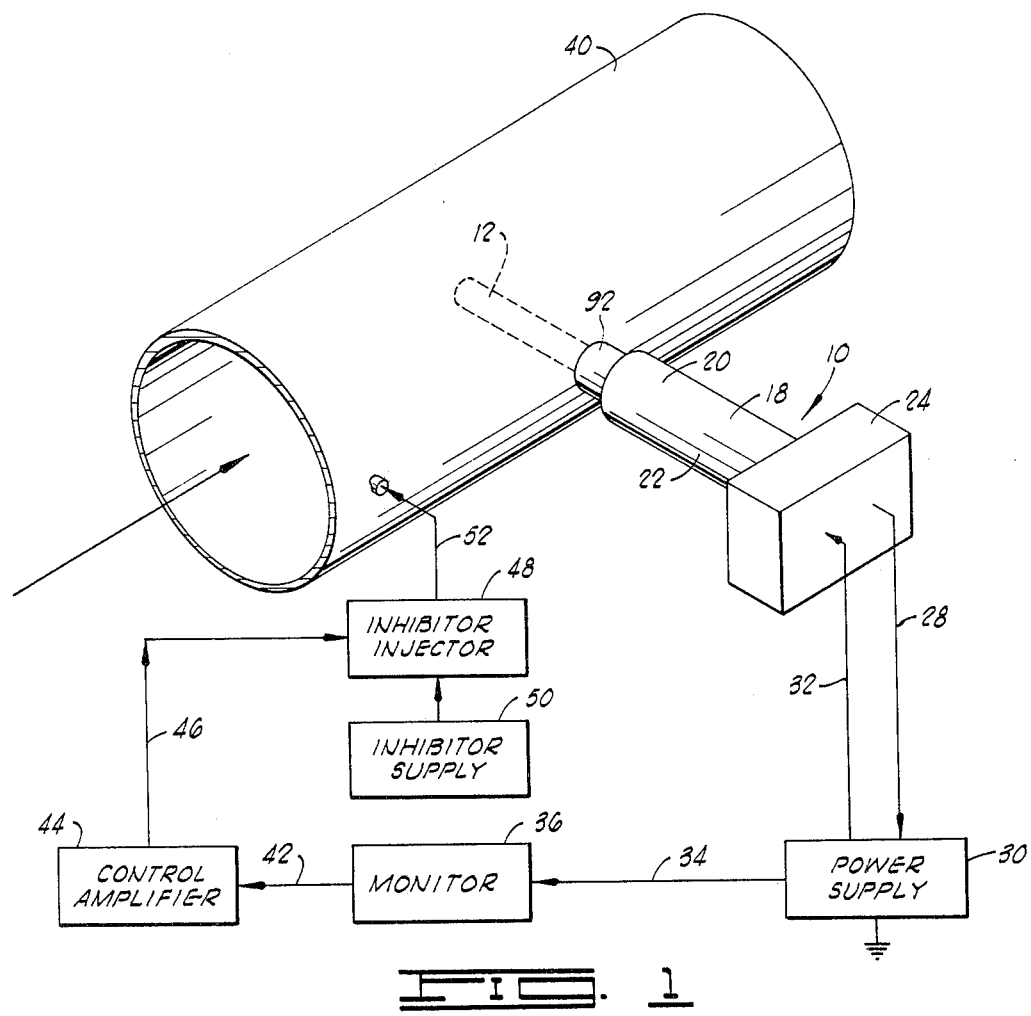
FIG. 1 is a perspective partially diagrammatic view of the portion of a pipeline having an improved diffusion monitoring apparatus of this invention operably connected thereto.
Figure 2:
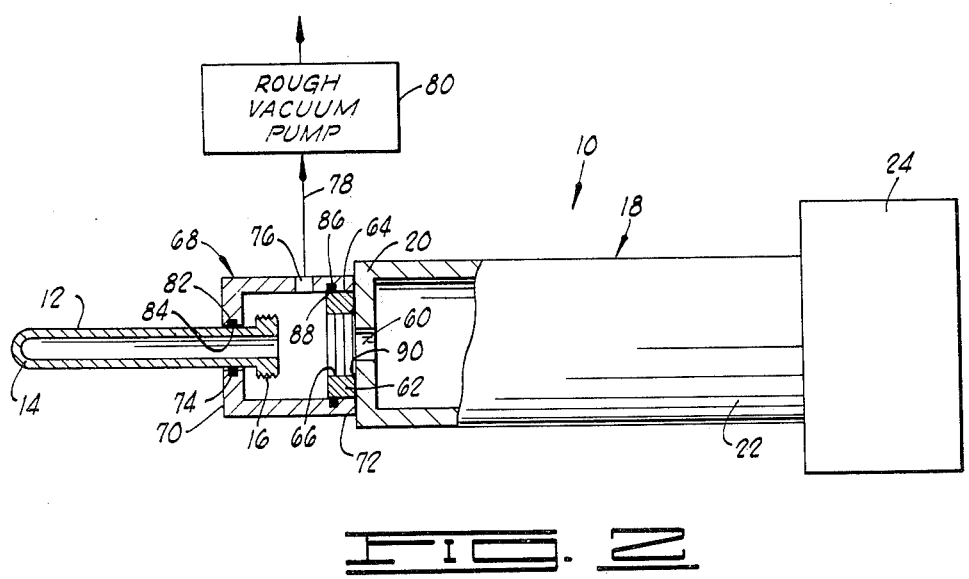
FIG. 2 is a side partly cross-sectional view of the diffusion monitoring apparatus of FIG. 1.

Referring now to the drawings, and particularly to FIGS. 1 and 2, one form of diffusion monitoring apparatus including the present invention is illustrated and generally designated by the numeral 10. The apparatus 10 is comprised of an elongated probe member 12 having a forward closed end 14 and an open rearward end 16. The probe is formed of a material having diffusion properties such that desired components contained in a fluid contacting the probe diffuse therethrough. As is well understood by those skilled in the art, the geometric design, size, thickness and the material of construction of the probe determine the diffusion rate of the selected component or components. In addition to materials which simply allow the diffusion of selected components classified as "passive" materials, other materials which are classified as "active" or "catalytic" can be used. "Active" materials are those which react with components in the fluid medium to produce the selected component to be monitored. "Catalytic" materials are those which catalyze a reaction of components in the fluid medium to produce the selected component. In the monitoring apparatus 10, the probe member 12, regardless of the particular configuration and type of material utilized, functions to generate or allow the diffusion of selected components into the hollow interior thereof. The rearward end 16 of the probe member 12 is formed into an enlarged annular flange portion and conventional threads are disposed around the peripheral sides thereof.

A collector chamber 18 is provided having a forward end 20 and a rearward end 22. An ion pump 24 is disposed on the collector chamber 18 at the rearward end 22 thereof. The collector chamber 18 and ion pump 24 can take any of a variety of forms and designs, and a variety of commercially available ion pumps commonly known as getter-ion pumps or magnetic-ion pumps can be utilized. Generally, the ion pump is comprised of an electronic system which includes a magnetic field in which free electrons are trapped. When the free gas molecules enter the magnetic field, they are ionized and accelerated by high electrical potential into an electrode where the ions are buried, thereby removing them from the evacuated interior. Some heavy gases cause sputtering of the cathode material, and this results in very chemically active surfaces inside the ion pump. Some gases are removed by chemical combination or gettering. For example, the ion pump can be comprised or a cold cathode of titanium or other suitable material at each end of a cylindrical anode having its axis aligned along the magnetic lines of force. An ion accelerating potential is supplied between the cathode and anode. Leads 28 and 32 are provided to supply a current path between the power supply 30 and ion pump 24. Thus, as ionized selected components contact and bury themselves in the cathode or cause a sputtering action, a current differential is generated exceedingly a predetermined background value which is derived from the power supply 30 by means of an electrical output lead 34 connected to a monitor 36. The monitor 36 can include any combination of indicators, recorders, alarms, or transmitters desired. In operation of the apparatus 10, the hollow interior of the probe member 12, the interior of the collector chamber 18, and the interior of the ion pump 24 are evacuated. The selected components which diffuse through the probe member 12 into the hollow interior thereof pass through the collector chamber and into the ion pump 24 where they are ionized and accelerated into contact with the cathode in the ion pump. In the special application depicted in FIG. 1, the diffusion monitoring apparatus 10 is installed in a pipeline 40 and used for monitoring the rate of corrosion in the pipeline and automatically injecting inhibitor thereinto so that the corrosion is maintained at a minimum. In this application, the probe member 12 is formed of a material such as carbon steel similar to the pipeline steel which allows atomic hydrogens produced by the corrosion of the probe material by the fluids flowing through the pipeline to diffuse therethrough. The electrical output generated by the apparatus 10 is directly proportional to the rate of diffused hydrogen which is in turn proportional to the corrosion rate in the pipeline. An electrical signal proportional to the signal generated by the monitoring apparatus 36 is led by way of a lead 42 to a control amplifier 44 which generates a control signal fed through a lead 46 to an inhibitor injector 48. The injector 48 can be a solenoid operated valve or other electrically operated apparatus which functions to cause inhibitor from a supply 50 thereof to be injected into the pipeline 40 by way of a conduit 52 connected thereto. Thus, in the corrosion monitoring application depicted in FIG. 1, the diffusion monitoring apparatus 10 monitors the presence of atomic hydrogen diffusion of the probe caused by corrosion of the probe material from corrosive fluid flowing through the pipeline 40 and brings about the injection of inhibitor into the fluid thereby controlling the corrosion at a desired low level.

As mentioned above, the diffusion monitoring apparatus, i.e., the interiors of the probe member 12 and collector chamber 18 are evacuated to permit the electronic operation of the getter ion pump which starts at a pressure at or below $10^{-3}$ torr. Heretofore, diffusion monitoring apparatus of this type have included an evacuation port in the probe member or in the collector chamber connected by a conduit to a shutoff valve or roughing valve which is in turn connected to a vacuum pump, commonly referred to as a roughing pump. By the present invention, improved apparatus is provided which eliminates the requirement for a roughing valve and provides positive sealing of the probe member 12 and collector chamber 18 after the evacuation thereof. More specifically, referring to FIG. 2, the collector chamber 18 includes a port 60 disposed in the forward end 20 thereof for communicating the interior of the collector chamber 18 with the interior of the probe member 12. A cylindrical connection member 62 is provided sealingly attached to the forward end 20 of the collector chamber 18 over the port 16 such as by welding so that the interior of the chamber 18 is communicated to the interior of the connection member 62. The connection member 62 includes conventional threads 64 disposed around the outside peripheral surfaces thereof and conventional threads 66 disposed in the interior surfaces thereof. The threads 66 and the interior of the connection member 62 are adapted to threadedly engage the threaded flange portion 16 of the probe member 12.

A removable housing 68 is provided having a forward end 70 and a rearward end 72. The rearward end 72 of the housing 68 includes an internally threaded opening adapted to threadedly engage the threads 64 of the connection member 62. The forward end 70 of the housing 68 includes an opening 74 through which the probe member 12 is slidably disposed. A connection 76 is provided in a side of the housing 68 connected by way of a conduit 78 to a vacuum or roughing pump means 80.

Means for providing a sliding seal between the opening 74 in the housing 68 and the outside peripheral surfaces of the probe member 12 are provided disposed within the opening 74. More specifically, a continuous annular groove is disposed in the internal sides of the opening 74 of the housing 68 and a resilient seal ring 84 is disposed in the groove 82. The seal ring 84 is of a size and shape such that it provides a sliding seal between the outside peripheral surfaces of the probe member 12 and the surfaces of the groove 82 in a conventional manner.

Means are provided for forming a seal between the outside peripheral surfaces of the connection member 62 and the internal sides of the rearward end 72 of the housing 68. That is, a continuous annular groove 86 is disposed in the interior of the threaded opening at the rearward end of the housing 68 positioned to lie opposite a flat unthreaded surface on the outside periphery of the connection member 62 when the housing 68 is threadedly connected to the connection member 62. A conventional resilient seal ring 88 is disposed in the groove 86 of a size and shape such that when the housing 68 is threaded onto the connection member 62 the seal ring 88 contacts the flat portion of the peripheral outside surface of the connection member 72 and the surfaces of the groove 86 providing a seal therebetween.

In operation of the diffusion monitoring apparatus 10, the apparatus is initially assembled as shown in FIG. 2 with the connection 76 of the housing 68 connected to the vacuum pump 80 by way of a conduit 78, and with the probe member 12 disconnected from the internal threads of the connection member 62. The vacuum pump 80 is operated to evacuate the internal portion of the probe member 12, the interior of the housing 68, and the collector chamber 18. Upon reaching a desired degree of vacuum within the apparatus 10 which will allow getter ion pump 24 to start operating, the probe member 12 is moved rearwardly so that the threaded flange portion 16 thereof contacts the connection member 62 and then rotated so that the flange portion 16 is threaded into the internal threads 66 of the connection member 62. A knife edge seal ring 90 is provided within the interior of the connection member 62 positioned adjacent the opening 60 in the forward end 20 of the collector chamber 18 for providing a seal between the collector chamber 18 and the rearward annular end surfaces of the probe member 12. As will be understood, the evacuation of the interiors of the probe member 12, housing 68 and collector chamber 18 is continued while the probe member 12 is threaded into the connection member 62 from the exterior of the housing 68 using a conventional wrench or other tool. Once the probe member 12 has been tightened against the knife edge seal ring 90 so that a seal is provided between the interior of the probe member 12 and the collector chamber 18, the operation of the vacuum pump 80 is terminated. The housing 68 is then removed from the apparatus 10 by disconnecting its threaded engagement with the threads 64 of the connection member 62 and sliding it over and off of the probe member 12. The apparatus 10 is next positioned with respect to the fluid system to be monitored so that the probe member 12 is exposed to and contacted by the fluid system. For example, as shown in FIG. 1, the probe member 12 can be inserted through a threaded connection 92 welded to the pipeline 40 with the threads 64 of the connection member 62 threadedly engaging the internal threads of the connection 92.

Figure 5:
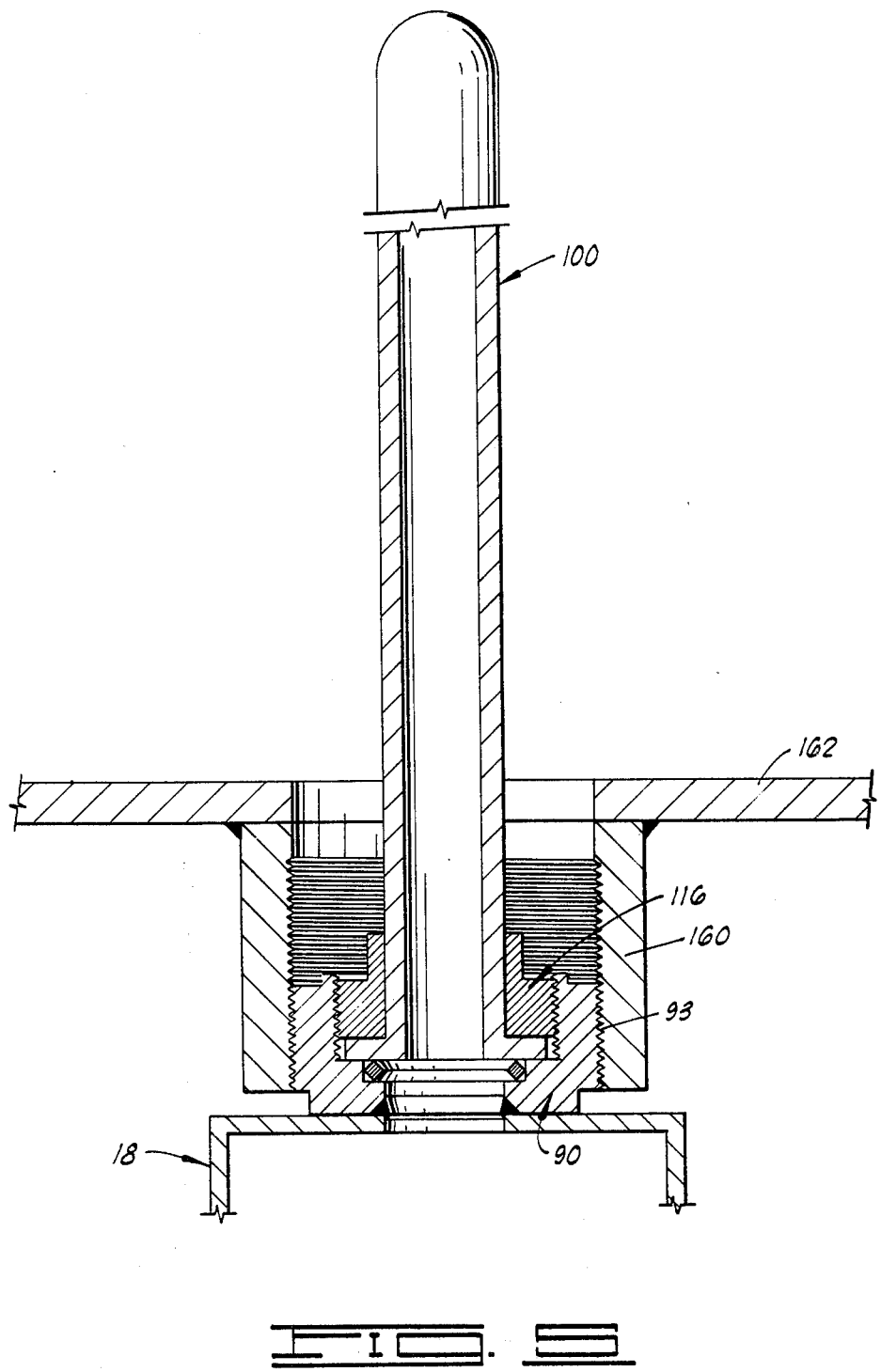
FIG. 5 is an enlarged side cross-sectional view of the apparatus of FIG. 3 showing the apparatus after partial disassembly and connection to a vessel or conduit.

Referring now to FIGS. 3, 4 and 5, an alternate embodiment of the apparatus of the present invention attached to the collector chamber 18, generally designated by the numeral 89, is illustrated. The apparatus 89 provides positive and adjustable sealing means between the outside peripheral surfaces of the probe member and the removable housing as well as eliminating the necessity that the flange portion of the probe member include threads. Further, the apparatus 89 allows the flange portion of the probe member to be prevented from rotating against a knife edge seal member when the probe member is sealingly connected to the collector chamber. Good vacuum practice dictates the use of a knife edge non-sliding seal for the permanent high vacuum needed for a low background signal current from the ion pump. This also allows the probe member to be formed of materials other than only those having strength characteristics capable of taking and holding threads.

Referring specifically to FIG. 3, the forward wall 20 of the collector chamber 18 is illustrated with a connection member 90 seal welded over the port 60 disposed therein. In this embodiment, the connection member 90 is substantially cylindrical in shape with threads 93 disposed around the outside peripheral surfaces thereof. A counterbore is provided in the top portion of the connection member 90 so that an upwardly facing internal annular shoulder 91 is provided in the internal lower portion thereof. The upper internal sides of the member 90 include threads 92 disposed thereon and an annular recess 94 is provided in the upwardly facing shoulder 91. A knife edge metal seal member 96 is disposed in the recess 94.

A probe member 100 is provided having an upper end 102 and a lower end 104. The lower end 104 is formed into an annular flange having a flat annular upwardly facing surface 106 and a flat annular downwardly facing surface 108. A removable cylindrical sleeve 110 having an upper end 112 and a lower end 114 is provided disposed over the lower portion of the probe member 100. The sleeve 110 is of an internal size such that it fits loosely against the outside peripheral surfaces of the probe member 100, and can be slidably removed therefrom. An annular threaded flange member 116 is also slidably positioned over the probe member 100 below the sleeves 110. The flange member 116 includes threads around the outside peripheral sides thereof adapted to threadedly engage the internal threads 92 of the connection member 90. The flange member 116 further includes a downwardly facing flat annular surface 118 which seats on and rests against the upwardly facing surface 106 of the flange portion 104 of the probe member 100. The lower end 114 of the sleeve 110 and the upper end 120 of the flange member 116 include overlapping cylindrical sections rigidly locked together by means of a lock bolt 122.

The upper end 112 of the sleeve 110 includes a packing gland assembly 124 for providing an adjustable sliding seal between the sleeve 110 and the outside peripheral surfaces of the probe member 100. More specifically, the assembly 124 is comprised of an internal annular recess 126 formed in the upper end 112 in the sleeve 110 with conventional annular packing material 128 disposed therein. Threads 130 are provided on the outside peripheral surfaces of the upper end 112 of the sleeve 110 and a packing compressor member 132 is provided threadedly engaging the threads 130 on the sleeves 110. As the packing compressor member 132 is threaded downwardly on the sleeve 110, the packing 128 is compressed and expanded outwardly resulting in a seal between the outside peripheral surfaces of the probe member 100 and the internal surfaces of the recess 126. When it is desired to remove the sleeve 110 from the probe member 100, the packing compressor member 132 is loosened which in turn loosens the packing 128 and allows the packing and sleeve to slide over the probe member 100.

A removable housing 134 is slidably disposed over the sleeve 110. A threaded counterbore 136 is disposed in the lower portion of the housing 134 for threadedly engaging the threads 93 disposed on the connection member 90. A second set of internal threads 138 are provided in the housing 134 having the same diameter and lead as the internal threads 92 of the connection member 90. A conventional annular seal member or gasket 140 is disposed between the upper end of the connection member 90 and the annular downwardly facing surface 142 formed within the housing 134 by the counterbore 136. When the housing 134 is threadedly engaged with the connection member 90, the seal member 140 is compressed between the upper end of the connection member 90 and the annular surface 142 of the housing 134 providing a seal therebetween.

A threaded connection 144 is provided in a side of the housing 134 for connection to vacuum pump means, and a packing gland assembly 146 is provided at the top end of the housing 134 for sealing the housing 134 against the outside peripheral surfaces of the sleeve 110. The packing gland assembly 146 is comprised of an internal recess 148 disposed in the top end of the housing 134 within which conventional annular packing material 150 is disposed. The outside peripheral surfaces of the top end of the housing 134 are provided with threads 152 and a conventional threaded packing compressor member 154 is threadedly disposed on the threads 152. As described above for the packing assembly 124, when the packing compressor member 154 is threaded downwardly on the housing 134, the packing material 150 is compressed providing a sliding seal between the housing 134 and the outside peripheral surfaces of the sleeve 110.

The sleeve 110 is further provided with a plurality of flat surfaces 160 positioned around the top outer surfaces thereof adjacent the top end 112 thereof. The flat surfaces 160 are provided for facilitating the rotation of the sleeve 110 and the threaded flange member 116 connected thereto using a conventional wrench or other similar tool.

In operation of the apparatus 89, it is assembled as illustrated in FIG. 4 with the sleeve 110, the threaded flange member 116 connected thereto and the probe member 100 in the uppermost position. That is, the threaded flange member 116 is rotated by rotating the sleeve 110 in a direction such that the flange member 116 is moved by the threads 138 to the uppermost position within the housing 134. A conduit is connected to the connection 144 of the housing 134 and to a vacuum pump means. As will be understood, the housing 134 is threaded tightly against the seal ring 140 so that a seal is provided thereby, and the packing gland assemblies 124 and 146 are tightened to provide seals between the housing 134, the sleeve 110 and the probe member 100. The vacuum pump means are operated to bring about the evacuation of the interiors of the probe member 100, the housing 134 and the collector chamber 18. Once the evacuation reaches a desired level, the sleeve 110 and flange member 116 attached thereto are rotated in a direction such that the flange member 116 is moved downwardly into engagement with the threads 92 within the interior of the connection member 90 so that the annular seating surface 108 of the flange portion 104 of the probe member 100 is moved into sealing contact with the knife edge seal ring 96 as shown in FIG. 3. Rotation of probe member 100 relative to edge seal 96 is prevented by restraining probe member 100 by use of suitable restraining means such as a wrench on flats (not shown) disposed in the outside surface of the top portion of probe member 100. During the rotation of the sleeve 110 and flange member 116 and the downward movement thereof, the vacuum pump means are continuously operated to maintain the evacuation of the apparatus 89.

Once the threaded flange member 116 has been firmly tightened so that the downwardly facing surface 108 of the probe member 100 sealingly contacts the seal ring 96, the vacuum pump means is disconnected from connecting means 144 and the packing gland assemblies 124 and 146 are loosened. The housing 134 is then removed from threaded engagement with the threads 93 of the connection member 90. After the housing 134 is removed, the lock bolt 122 which locks the sleeve 110 and threaded flange member 116 together is loosened and the sleeve 110 is removed from the probe member 100.

After evacuation of the apparatus 89 and removal of the housing 134 and sleeve 110, and as is shown in FIG. 5, the probe member 100 can be inserted through a threaded connection 160 in a pipeline or vessel 162 containing the fluid to be monitored, and the threads 93 of the connection member 90 threadedly engaged with the internal threads of the connection 160.

Thus, the present invention is well adapted to carry out the objects and attain the ends and advantages mentioned as well as those inherent therein. While presently preferred embodiments have been described for the purpose of this disclosure, numerous changes in the construction and arrangement of parts will be readily apparent to those skilled in the art which are encompassed within the lawful scope of the appended claims.

What is claimed is:

1. In a monitoring apparatus which includes an evacuated elongated hollow probe member through which components to be monitored diffuse, an evacuated collector chamber sealingly connected to the rearward end of said probe member and an ion pump means connected to said chamber for providing an electrical current output in proportion to the rate of diffusion of said components, the improvement which comprises:

said collector chamber including a port for communicating the interior thereof with the interior of said hollow probe member;

a cylindrical connection member sealingly attached to said chamber around said port, said connection member having threads disposed around the outside peripheral surfaces thereof and within the interior surfaces thereof;

the rearward end of said probe member being of a size and including threads disposed thereon for threadedly engaging the threads within the interior of said connection member;

a housing having a forward end and a rearward end, the rearward end including a first threaded opening adapted to threadedly engage the threads disposed around the outside peripheral surfaces of said connection member and the forward end including a second opening therein through which said elongated probe member is slideably disposed, said housing further including a third opening therein for connection to vacuum pump means so that the interiors of said housing, said chamber and said probe member can be evacuated with said probe member disconnected from said connection member, said probe member then threadedly connected to said connection member from the exterior of said housing while maintaining said evacuation and said housing subsequently removed from said connection member and said probe member; and means disposed in said second opening in said housing for providing a sliding seal between said housing and the outside peripheral surfaces of said probe member.

2. The apparatus of claim 1 wherein said means for providing a sliding seal between said housing and the outside peripheral surfaces of said probe member comprises:

said second opening of said housing including a continuous groove disposed in the internal sides thereof, said groove lying in a plane transverse to the axis of said elongated probe member; and a resilient seal member disposed in said groove, said seal member being of a size and shape such that a seal is provided thereby between the peripheral surfaces of said probe member and the surfaces of said groove.

3. The apparatus of claim 2 which is further characterized to include means attached to said housing for providing a seal between the rearward end thereof and said connection member when said housing is threadedly connected to said connection member.

4. The apparatus of claim 3 which is further characterized to include means disposed between the rearward end of said probe member and the interior of said connection member for providing a knife edge seal therebetween when said probe member is threadedly connected to said connection member.

5. Apparatus for connecting the open end of an elongated hollow probe member to a chamber whereby the interiors of said probe member and said chamber can be evacuated while said probe member and chamber are disconnected from each other and then said probe member sealingly connected to said chamber while maintaining said evacuation comprising:

said chamber including a port for communicating the interior thereof with the interior of said probe member;

an annular connection member sealingly attached to said chamber around said port, said connection member including threads disposed on the inside and outside annular surfaces thereof;

said open end of said probe member including threads thereon adapted for threadedly engaging the threads on the inside annular surfaces of said connection member;

a removable housing having a forward end aand a rearward end, the rearward end including a first threaded opening adapted to threadedly engage the threads on the outside annular surfaces of said connection member and the forward end including a second opening therein through which said probe member is slidably disposed, said housing further including a third opening therein for connection to vacuum pump means; and means disposed in said second opening in the forward end of said housing for providing a sliding seal between said housing and the outside peripheral surfaces of said probe member so that said probe member can be selectively threadedly disconnected from or connected to said connection member from the exterior of said housing, said probe member and said chamber evacuated.

6. The apparatus of claim 5 wherein said means for providing a seal between said housing and the outside peripheral surfaces of said probe member comprise:

said second opening in said housing including a continuous groove disposed in the internal sides thereof; and a resilient seal member disposed in said groove, said seal member being of a size and shape such that a seal is provided thereby between the peripheral surfaces of said probe member and the surfaces of said groove.

7. The apparatus of claim 6 which is further characterized to include means attached to said housing for providing a seal between the rearward end thereof and said connection member when said housing is threadedly connected to said connection member.

8. The apparatus of claim 7 which is further characterized to include means disposed between the rearward end of said probe member and the interior of said connection member for providing a high vacuum type seal therebetween when said probe member is threadedly connected to said connection member.

9. Apparatus for connecting the open end of an elongated hollow probe member to a chamber whereby the interiors of said probe member and said chamber can be evacuated while said probe member and chamber are disconnected from each other and said probe member then sealingly connected to said chamber while maintaining said evacuation comprising:

said chamber including a port for communicating the interior thereof with the interior of said probe member;

an annular connection member sealingly attached to said chamber over said port so that said port communicates with the interior of said connection member, said connection member including threads disposed on the outside peripheral surfaces thereof and on the interior surfaces thereof, and further including an upwardly facing annular seating surface in the interior thereof below said threads disposed therein;

said open end of said probe member including an annular flange portion providing upwardly and downwardly facing annular surfaces and being adapted to fit within the interior of said connection member with said downwardly facing annular surface positioned against the upwardly facing annular seating surface within said connection member;

an elongated sleeve having an upper end and a lower end adapted to fit over the lower outside peripheral surfaces of said probe member with the lower end thereof resting against said upwardly facing annular seating surface of said flange portion of said probe member, said elongated sleeve including an annular threaded flange portion at the lower end thereof adapted to threadedly engage the threads disposed on the interior surfaces of said connection member;

means attached to the upper end of said sleeve member for providing a seal between said sleeve member and the outside peripheral surfaces of said probe member;

a housing having an upper end and a lower end, the lower end including a first set of internal threads adapted to threadedly engage the threads disposed on the outside peripheral surfaces of said connection member and the upper end including an opening therein through which said probe member and said sleeve are slidably disposed, said housing further including an opening in a side thereof for connection to vacuum pump means, and means attached to the upper end of said housing for providing a sliding seal between said housing and the outside peripheral surfaces of said sleeve.

10. The apparatus of claim 9 wherein said elongated sleeve is further characterized to include connection means between said annular threaded flange portion thereof and the upper end portion thereof whereby the upper end portion can be disconnected from said threaded flange portion and removed from said probe member.

11. The apparatus of claim 10 wherein said housing is further characterized to include a second set of internal threads positioned above said first set of internal threads and being adapted to threadedly engage said threaded flange portion of said sleeve so that said threaded flange portion can be threadedly moved from the internal threads in said connection member to the second set of internal threads in said housing and from the second set of internal threads in said housing into the interior threads in said connection member by the selective rotation of said sleeve.

12. The apparatus of claim 11 which is further characterized to include means for providing a seal between said housing and said connection member disposed within said housing between said housing and said connection member.

13. The apparatus of claim 12 which is further characterized to include means for providing a knife edge seal between the downwardly facing annular surface of said flange portion of said probe member and the upwardly facing annular surface within the interior of said connection member disposed between said annular surfaces.

* * * * *